(12) United States Patent
Oakey

(10) Patent No.: US 6,637,239 B2
(45) Date of Patent: Oct. 28, 2003

(54) NITROGEN REJECTION METHOD AND APPARATUS

(75) Inventor: John Douglas Oakey, Godalming (GB)

(73) Assignee: The BOC Group plc, Windlesham (GB)

( * ) Notice: Subject to any disclaimer, the term of this patent is extended or adjusted under 35 U.S.C. 154(b) by 0 days.

(21) Appl. No.: 10/192,452

(22) Filed: Jul. 10, 2002

(65) Prior Publication Data
US 2003/0029191 A1 Feb. 13, 2003

(30) Foreign Application Priority Data
Jul. 11, 2001 (GB) .............................. 0116977

(51) Int. Cl.$^7$ ................................. F25J 3/00; F25J 3/02
(52) U.S. Cl. ........................................ 62/620; 62/927
(58) Field of Search ........................ 62/620, 927, 617, 62/630

(56) References Cited

U.S. PATENT DOCUMENTS

| | | | | |
|---|---|---|---|---|
| 4,415,345 A | * | 11/1983 | Swallow | ...................... 62/630 |
| 5,220,797 A | * | 6/1993 | Krishnamurthy et al. | ..... 62/620 |
| 6,227,005 B1 | * | 5/2001 | Higginbotham et al. | ...... 62/646 |

* cited by examiner

Primary Examiner—William C. Doerrler
(74) Attorney, Agent, or Firm—Philip H. Von Neida

(57) ABSTRACT

Nitrogen is rejected from a feed gas stream comprising methane and nitrogen so as to form a methane product. The feed gas stream is cooled in a main heat exchanger and is rectified in a double rectification column comprising a higher pressure rectification column, a lower pressure rectification column, and a condenser-reboiler placing the higher pressure rectification column in heat exchange relationship with the lower pressure rectification column. At least part of the feed gas stream is expanded into the higher pressure rectification column through an expansion valve, the feed gas stream being partially liquefied upstream of the double rectification column. Over a period of time the mole fraction of nitrogen in the feed gas mixture increases. At a suitable increased nitrogen mole fraction, operation of a second double rectification column in parallel with the first double rectification column is commenced.

10 Claims, 1 Drawing Sheet

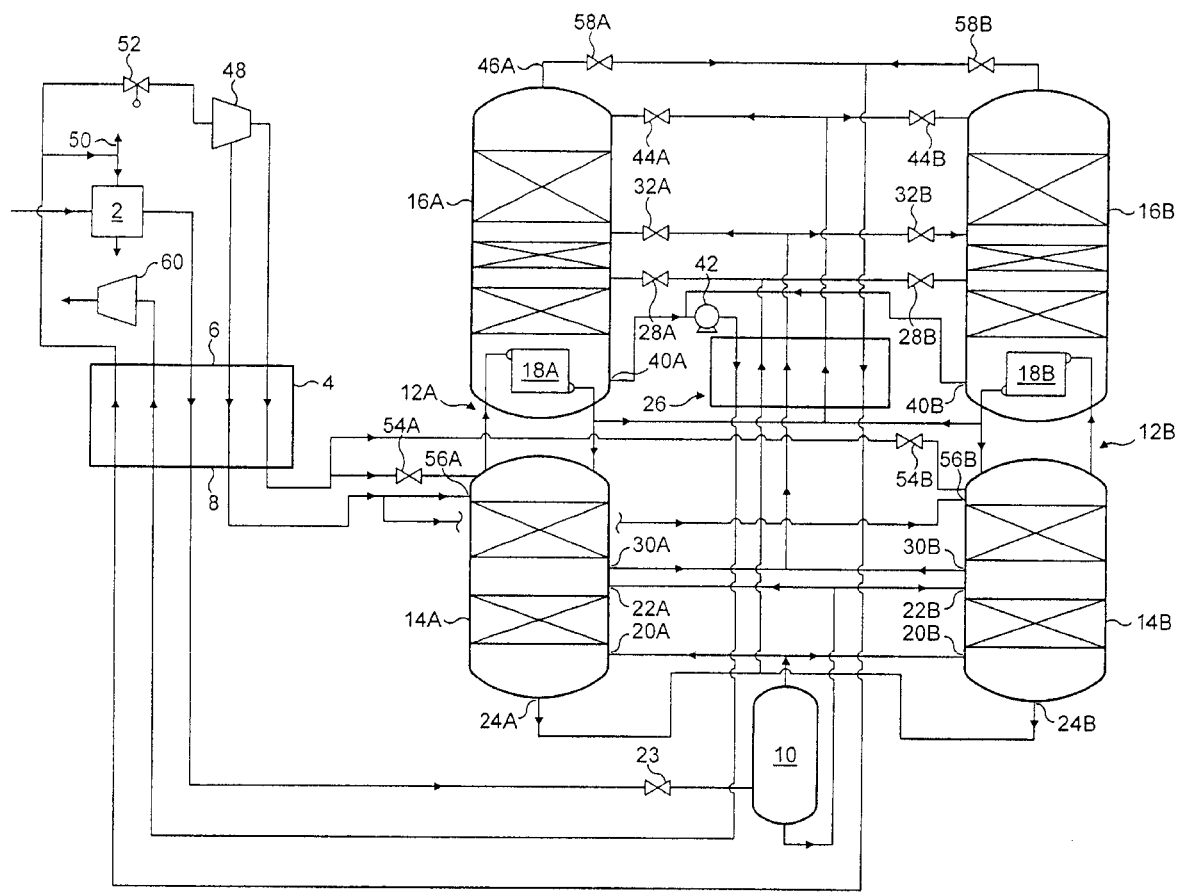

US 6,637,239 B2

NITROGEN REJECTION METHOD AND APPARATUS

FIELD OF THE INVENTION

This invention relates to a method of and apparatus for rejecting nitrogen from a feed gas stream comprising methane and nitrogen so as to form a methane product.

BACKGROUND OF THE INVENTION

It is known to extract natural gas from underground reservoirs. The natural gas often contains nitrogen. The nitrogen may be in part or totally derived from nitrogen which has been injected into the reservoir as part of an enhanced oil recovery (EOR) or enhanced gas recovery (EGR) operation. A feature of such operations is that the concentration of nitrogen in the natural gas tends to increase with the passage of time from about 5% by volume to about 60% by volume.

U.S. Pat. No. 4,415,345 discloses a process for rejecting the nitrogen from the methane in a double rectification column operating at cryogenic temperatures. A double rectification column comprises a higher pressure rectification column, a lower pressure rectification column, and a condenser-reboiler placing the top of the higher pressure rectification column in indirect heat exchange relationship with a region, usually the bottom, of the lower pressure rectification column. In the process according to U.S. Pat. No. 4,415,345 a stream of a mixture of nitrogen and methane is cooled at elevated pressure to a temperature suitable for its separation by rectification. A part of the feed gas is liquefied. The resulting gas mixture is separated by rectification in a lower pressure rectification column having a condenser-reboiler operatively associated with a bottom region thereof. The reboiling passages of the condenser-reboiler are heated by pressurised nitrogen. Typically, a part of the nitrogen is separated in a higher pressure rectification column and another part flows in a heat pump circuit to and from the top of the lower pressure rectification column. At low nitrogen levels in the feed gas, the higher pressure rectification column is by-passed and all the nitrogen for the condenser-reboiler flows in the heat pump circuit, which is separate from the main heat exchanger used to cool the feed gas stream. As the nitrogen content in the feed gas gradually increases so the higher pressure column is used to provide some of the nitrogen. Eventually, the heat pump circuit is closed and the higher pressure column produces all the nitrogen.

The higher pressure rectification column used in the process according to U.S. Pat. No. 4,415,345 is operated with a second condenser-reboiler at its bottom. As a consequence, there is a high vapour flow therethrough and it needs to be of a relatively large diameter even though it is operated at maximum capacity only at high nitrogen concentrations.

It is an aim of the present invention to provide a method and apparatus that keeps down the vapour traffic through the higher pressure rectification column and thereby makes it possible to keep down the diameter of this column.

SUMMARY OF THE INVENTION

According to the present invention there is provided a method of rejecting nitrogen from a feed gas stream comprising methane and nitrogen so as to form a methane product, the mole fraction of nitrogen in the feed gas increasing over a period of time. The method comprises cooling the feed gas stream in a main heat exchanger, and rectifying the cooled feed gas stream in a first double rectification column comprising a higher pressure rectification column, a lower pressure rectification column, and a condenser-reboiler placing the higher pressure rectification column in heat exchange relationship with the lower pressure rectification column, expanding at least part of the feed gas stream into the higher pressure rectification column, partially liquefying the feed gas stream upstream of the first double rectification column, and operating a second double rectification column in parallel with the first double rectification column when the nitrogen mole fraction in the feed gas stream has increased to at least a predetermined value.

The invention also provides apparatus for rejecting nitrogen from a feed gas stream comprising methane and nitrogen so as to form a methane product, the apparatus comprising a main heat exchanger for cooling the feed gas stream, a first double rectification column for rectifying the feed gas stream comprising a higher pressure rectification column, a lower pressure rectification column, and a condenser-reboiler placing the higher pressure rectification column in heat exchange relationship with the lower pressure rectification column, and an expansion device downstream of the main heat exchanger communicating with the higher pressure rectification column, the expansion device being arranged so as, in use, to introduce a part of the feed gas stream into the higher pressure rectification column in liquid state, characterised in that there is a second double rectification column in parallel with the first double rectification column.

As the mole fraction of nitrogen in the feed gas mixture becomes greater with the passage of time, so the flow of product methane becomes less, and so less of the feed gas mixture is liquefied against the reduced flow of the product stream. In consequence, there is a tendency for an ever increasing proportion of the feed gas mixture to enter the higher pressure rectification column in vapour state with the passage of time. Thus, in its normal operating lifetime, which may well exceed ten years or more, and last until the reservoir which is the source of the feed gas mixture is effectively exhausted, the first double rectification column may have to cope with a very wide range of vapour loadings, posing considerable design problems.

The obvious solution to these problems would be to arrange for all the feed gas mixture to enter the higher pressure rectification column in vapour state. Therefore, changes in the composition of the feed gas mixture would not substantially affect the vapour loading of the higher pressure rectification column. However, one disadvantage of such a procedure, is that the vapour loading of the higher pressure rectification column would always be at a maximum.

The method and apparatus according to the invention make it possible, however, to reduce the effective range of vapour loadings that both rectification columns of the first double rectification column have to face during their operating lifetime by providing a second double rectification column in parallel with the first double rectification column, which second double rectification column can be brought into operation at a suitable nitrogen mole fraction. Accordingly, if the vapour loading on either column of the first double rectification column approaches a level at which its performance would become unsatisfactory, the second double rectification column may be used to share the load. Typically, the apparatus according to the present invention may be installed as a complete unit. Alternatively the second double rectification column may be retrofitted to the first double rectification column whenever the latter is approaching an operational stage at which either rectification column is overloaded with vapour. The latter alternative offers the advantage that the initial size, complexity and cost of the apparatus according to the invention can be kept down.

Preferably, the operating pressure of the higher pressure column of the first double rectification column is periodically increased. To this end, the lower pressure column of the first double rectification column preferably has a back pressure regulating valve associated with it which is operable to increase the pressure therein. Increasing the operating pressure of the lower pressure rectification column brings about a concomitant increase in the operating pressure of the higher pressure rectification column. Increasing the operating pressure of the higher pressure rectification column enables it to receive more vapour per unit time for operation at a given constant percentage of flood. In addition, increasing the operating pressure of the higher pressure rectification column tends to increase the proportion of the feed gas mixture that passes out of the expansion device in liquid state. These two factors enable the method and apparatus according to the invention to be operated at higher feed gas nitrogen mole fractions without using the second double rectification column than would otherwise be possible.

Preferably, particularly when the mole fraction of nitrogen in the feed gas mixture is less than 0.15, a first flow of gas is passed as a first recycle gas flow from the lower pressure rectification column of the first double rectification column to the higher pressure rectification column of the first double rectification column. The first recycle gas flow is compressed, is cooled in the main heat exchanger, is liquefied in a condenser-reboiler, and is introduced into the higher pressure rectification column. This counteracts a tendency for the double rectification column to be short of reflux when the mole fraction of nitrogen in the feed gas mixture is relatively low, particularly when it is 0.15 or less.

A product methane stream is preferably withdrawn in liquid state from the lower pressure rectification column of the first double rectification column, is raised in pressure, and is vaporised at least in part in the main heat exchanger. A second recycle gas flow from the lower pressure rectification column is preferably compressed, is cooled in the main heat exchanger, and is introduced at least partly in liquid state into the top of the higher pressure rectification column via a second expansion device. Preferably the second recycle flow is compressed to a higher pressure than the first recycle flow, the higher pressure typically being a supercritical pressure. More preferably, the first and second recycle flows are compressed in the same plural stage compressor, the second recycle flow being taken from a stage of the compressor downstream of the one from which the first recycle flow is taken.

It is, however, possible to use separate compressors for these purposes, or indeed to take all the compressed recycle gas at the same pressure and pass it through the same second expansion device. In this latter arrangement a two phase fluid flow passes out of the second expansion device with the vapour part of the two phase flow constituting the first recycle gas stream and the liquid part of the two phase flow constituting the second recycle flow. All these arrangements make it possible for the temperature-enthalpy profile of the streams being cooled in the main heat exchanger to be kept as close match to the temperature-enthalpy profile of the streams being warmed in the main heat exchanger. As a result the main heat exchanger can be operated at a good thermodynamic efficiency.

The back pressure regulating valve is preferably operably associated with means for changing its setting in response to an increase in the mole fraction of nitrogen in the feed gas mixture. If desired, the control means may make use of an algorithm relating the optimum operating pressure of the lower pressure rectification column to the mole fraction of nitrogen in the feed gas mixture. Alternatively, and more preferably, the pressure regulating valve may be controlled so as to maintain a constant percentage recovery of methane in the product gas.

Preferably, a vent stream is taken from the first recycle gas flow upstream of its compression and is vented from the method and apparatus according to the invention.

Preferably, there is a flow control valve operable to control the size of the first recycle flow.

The pressurised liquid product methane stream is preferably warmed, without being vaporised, in a further heat exchanger upstream of its vaporisation in the main heat exchanger.

Preferably, all the bottom fraction obtained in the higher pressure rectification column of the first double rectification column is withdrawn therefrom and is sent to the lower pressure rectification column. There is therefore no reboiling of this fraction in the higher pressure rectification column.

BRIEF DESCRIPTION OF THE DRAWING

The method according to the invention will now be described by way of example with reference to the accompanying drawing which is a schematic flow diagram of a nitrogen rejection plant.

The drawing is not to scale.

DETAILED DESCRIPTION OF THE INVENTION

A stream of natural gas or gaseous nitrogen-methane mixture is recovered by known means not forming part of this invention from an underground oil or gas reservoir. The stream is typically recovered at a pressure in the order of 40 bar absolute. The stream may be subjected to preliminary treatment (not shown) in order to remove any hydrogen sulphide or other sulphur-containing impurity therefrom. Such purification of natural gas is well known in the art and need not be referred to in further detail herein. After removal of any such hydrogen sulphide impurity, the elevated pressure methane-nitrogen stream still typically contains water vapour impurity. The water vapour is removed by passage through a purification unit 2. The purification unit 2 preferably comprises a plurality of adsorption vessels containing adsorbent able selectively to adsorb water vapour from the feed gas stream. Such purification units typically operate on a pressure swing adsorption or a temperature swing adsorption cycle, the latter generally being preferred. If the feed gas stream also contains carbon dioxide impurity, the purification unit can additionally contain an adsorbent selected for carbon dioxide so as to effect the carbon dioxide removal.

The resulting purified feed gas stream now consisting essentially of nitrogen and methane flows through a main heat exchanger 4 from its warm end 6 to its cold end 8. The main heat exchanger 4 comprises a plurality of heat exchange blocks preferably joined together to form a single unit. Downstream of the main heat exchanger 4, the feed gas stream is expanded through a throttling valve 23 into a phase separator 10. Depending on its pressure, the feed gas stream either becomes liquid in the main heat exchanger 4 or on expansion through the throttling valve 23. Typically, depending on its composition, at least 75 mole per cent of the feed gas stream is liquefied.

The remaining vapour forms a feed stream to a double rectification column. In the drawing first and second double rectification columns 12A and 12B respectively are shown. The columns 12A and 12B are arranged in parallel with each other. When the plant shown in the drawing first comes into service, there is no flow communication of the incurring feed gas stream with the second double rectification column 12B. Instead all the moving feed gas is fed to the first double rectification column 12A. It is only when the higher pressure rectification column 14A is approaching overload with vapour that the second double rectification column 12B is employed. Stop valves (not shown) are provided so as to enable the double rectification column 12B to be isolated from the feed gas supply until it is required to assist the double rectification column 12A in separating the feed gas mixture.

The vapour is disengaged from the liquid in the phase separator 10. A stream of the vapour phase flows from the top of the phase separator 10 through an inlet 20A into the bottom region of a higher pressure rectification column 14A forming part of the double rectification column 12A with a lower pressure rectification column 16A and a condenser-reboiler 18A thermally linking the top of the higher pressure rectification column 14A to the bottom of the lower pressure rectification column 16A. A stream of the liquid phase flows from the bottom of the phase separator 10 into an intermediate mass exchange region of the higher pressure rectification column 14A through another inlet 22A. Typically the feed gas stream enters and leaves the purification unit 2 at a pressure well in excess of the operating pressure of the higher pressure rectification column 14A. The temperature drop resulting from the expansion of the feed stream has the consequence that there is typically no need to supply an external source of refrigeration. The expansion therefore meets most of the refrigeration requirements of the method according to the invention and as a result there is typically no need to supply any turbo-expander for this purpose.

The feed gas mixture is separated in the higher pressure rectification column 14A into a vaporous nitrogen top fraction and a liquid methane-enriched bottom fraction. A stream of the methane enriched bottom fraction is withdrawn from the higher pressure rectification column 14A through a bottom outlet 24A and is sub-cooled by passage through a further heat exchanger 26. The resulting sub-cooled methane-enriched liquid stream flows through a throttling valve 28A and is introduced into an intermediate mass exchange region of the lower pressure rectification column 16A. In addition, a liquid stream comprising methane and nitrogen is withdrawn from an intermediate mass exchange region of the higher pressure rectification column 14A through an outlet 30A, is sub-cooled by passage through the further heat exchanger 26, is passed through a throttling valve 32A and is introduced into a second intermediate mass exchange region of the lower pressure rectification column 16A located above the first intermediate mass exchange region.

The streams comprising methane and nitrogen are separated in the lower pressure rectification column 16A in order to form a top nitrogen vapour fraction and a bottom product liquid methane fraction. A stream of the bottom fraction is withdrawn through an outlet 40A from the lower pressure rectification column 16A and is raised in pressure by operation of a pump 42. The resulting pressurised product liquid methane stream is passed through the further heat exchanger 26 countercurrently to the streams being sub-cooled therein.

The pressurisation of the product liquid methane stream has the effect of raising its pressure above its saturation pressure. Thus, in effect, the pressurised liquid methane product stream is in sub-cooled state as it enters the further heat exchanger 26. It is warmed in the further heat exchanger 26 to remove the sub-cooling. Preferably, no vaporisation of the liquid methane product stream takes place in the further heat exchanger 26. The warmed liquid methane product stream passes from the heat exchanger 26 through the main heat exchanger 4 from its cold end 8 to its warm end 6. It is vaporised as it passes through the main heat exchanger 4. The vaporised methane product is compressed to a desired product delivery pressure in a product compressor 60.

Reflux for the higher pressure rectification column 14A and the lower pressure rectification column 16A is formed by taking nitrogen vapour from the top of the higher pressure rectification column 14A and condensing it in the condensing passages of the condenser-reboiler 18A. A part of the resulting condensate is returned to the higher pressure rectification column 14A as reflux. The remainder is sub-cooled by passage through the further heat exchanger 26 and is passed through a throttling valve 44A into the top of the lower pressure rectification column 16A and therefore provides liquid reflux for that column.

A nitrogen vapour stream is withdrawn from the top of the lower pressure rectification column 16A through an outlet 46A and is warmed by passage through the further heat exchanger 26. The resulting warmed nitrogen stream is further warmed to approximately ambient temperature by passage through the main heat exchanger 4 from its cold end 8 to its warm end 6. The warmed nitrogen flow is divided into three sub-streams. One sub-stream is compressed in a recycle compressor 48 having a plurality of stages. A second sub-stream of the warmed nitrogen from the main heat exchanger 4 is employed in the regeneration of the adsorbent beds in the purification unit 2. A third sub-stream of the nitrogen is vented to atmosphere through a vent pipeline 50 as a waste stream. The relative size of the recycle stream is determined by the position of an adjustable flow control valve 52 on the inlet side of the recycle compressor 48.

The recycle gas flow entering the compressor 48 is divided into two parts. One stream passes through all the stages of the compressor and flows through the main heat exchanger 4 from its warm end 6 to its cold end 8. The resulting cooled stream of nitrogen is returned to an upper region of the higher pressure rectification column 14A through a throttling valve 54A. The nitrogen is typically compressed to a supercritical pressure in the recycle compressor 48 and is cooled in the main heat exchanger 4 to a temperature sufficiently low for it to be liquefied by expansion through the throttling valve 54A. The flow of this part of the recycle gas through the main heat exchanger 4 helps to match the composite temperature-enthalpy profile of the streams being cooled in the main heat exchanger 4 more closely to that of the streams being warmed therein.

An intermediate pressure stream can also be withdrawn from the compressor 48 and is cooled by passage through the main heat exchanger 4 from its warm end 6 to its cold end 8. The intermediate pressure gas remains in gaseous state as it passes through the main heat exchanger 4 from its warm end 6 to its cold end 8. The intermediate pressure nitrogen is introduced into an upper region of the higher pressure rectification column 14A through an inlet 56A. The intermediate pressure is therefore chosen to be essentially the operating pressure of the higher pressure rectification column 14A. In an alternative arrangement, this intermediate pressure stream can also be introduced directly to the condenser-reboiler 18A (not shown in the FIGURE), with the resulting condensate being returned to the higher pressure rectification column 14A as reflux.

The part of the recycle gas that flows from the lower pressure rectification column 16A to the higher pressure rectification column 14A via the inlet 56A performs a heat pumping duty which enhances the production of liquid reflux for the rectification columns 14A and 16A.

Initially, the purified feed gas stream typically contains about 95 mole per cent of methane and 5 mole per cent of nitrogen. The lower pressure rectification column 16A is operated at a pressure at its bottom of about 1.9 bar absolute. This sets the temperature at which the bottom fraction in the lower pressure rectification column boils. This temperature is one or two degrees Kelvin lower than the temperature at which the nitrogen top fraction separated in the higher pressure rectification column 14A is condensed in the condensing passages of the condenser-reboiler 18A. As a result, the pressure in the lower pressure rectification column 16A sets the condensing pressure in the condenser-reboiler 18A and hence the operating pressure at the top of the higher pressure rectification column 14A. When the pressure at the bottom of the lower pressure rectification column 16A is in the order of 1.9 bar absolute, the operating pressure at the top of the higher pressure rectification column is in the order of 17 bar absolute. Increasing the pressure at the bottom of the lower pressure rectification column 16A has the effect of producing a resultant increase in the operating pressure at the top of the higher pressure rectification column 14A.

The pressure in the lower pressure rectification column 16A is controlled by a back pressure regulating valve 58A in the outlet 46A for nitrogen from the lower pressure rectification column 16A. The back pressure regulating valve 58A in controlling the pressure in the lower pressure rectification column 16A effectively controls the pressure at the top of the higher pressure rectification column 14A. At first, the back pressure regulating valve 58A is typically arranged to be in a fully open or non-regulating position.

Methane is considerably less volatile than nitrogen. The initial feed gas composition is therefore relatively easy to liquefy as it contains a preponderance of methane. Typically, with a feed pressure of 40 bar absolute and a higher pressure rectification column 14 operating pressure of about 22 bar absolute, in the order of 75% by volume or more of the feed gas can be liquefied. The liquefaction of such a high proportion of the feed gas stream substantially reduces the vapour loading on the higher pressure rectification column 14A in comparison with what it would be if none of the feed gas stream were liquefied.

In a typical enhanced oil recovery or enhanced gas recovery operation, the proportion of nitrogen in the feed gas mixture gradually increases over the operating life of the well from about 5 mole per cent to 60 mole per cent. As the proportion of nitrogen increases in the feed gas mixture, it becomes more difficult to liquefy and hence the proportion of liquid in the fluid exiting the valve 23 gradually decreases. This has the effect of increasing the vapour loading on the higher pressure rectification column 14A even though the volumetric flow rate of the feed gas mixture remains unaltered.

It is customary to design a distillation column so that at maximum specified vapour loading it operates quite close to its flood point, say, at 80 to 90% of flood. The increase in the vapour loading that would take place as the mole percentage of nitrogen in the feed gas mixture increases from 5 to 60% is well in excess of that which would cause the column 14A to flood were its diameter to be selected such as to cause it to operate close to the flood point when the nitrogen mole percentage is at the bottom of its range. The effect of increasing nitrogen mole fraction in the feed gas can to some extent be mitigated by initially operating the higher pressure rectification column 14A at a lower vapour loading than 80% of flood and thereby increase the hydraulic operating range of the column.

The ability to turn down a liquid-vapour contact column depends on the choice of column internals to effect mass exchange between ascending vapour and descending vapour. In general, structured packing offers a greater degree of turndown than conventional liquid-vapour contact trays, be they of the bubble cap or sieve type. Accordingly, if structured packing is employed in the higher pressure rectification-column 14, this column can be operated with a vapour loading of, say, about 50% of the flood point when the initial nitrogen mole fraction in the natural gas is 0.1. Even so, since the vapour loading is likely to increase more than twofold during the lifetime of the enhanced oil recovery or enhanced gas recovery operation, this measure of itself is unlikely to be entirely satisfactory. Further, it may be economically disadvantageous to build a column 14 which is initially considerably oversized if it is to be operated for several years at substantially less than an optimum vapour loading.

The apparatus shown in the drawing enables this problem to be mitigated by making use of the back pressure regulating valve 58A to control the pressure in the lower pressure rectification column 16A and hence the pressure in the higher pressure rectification column 14A so as to compensate for increasing nitrogen mole fraction in the higher pressure rectification column 14A. In one arrangement the mole fraction of methane in the feed gas stream (either upstream or downstream of the purification unit), the mole fraction of methane in the product stream withdrawn from the outlet 40A, and the flow rate of the product stream are all monitored and the percentage recovery of methane automatically calculated by appropriate process control software. The arrangement is such that the automatically calculated value of the methane recovery is used to control the setting of the back pressure regulating valve 58A. In one embodiment, a control means is connected to the back pressure regulating valve 58A for maintaining a constant percentage recovery of methane in the product gas. The control means may, for example, comprise a controller and associated software known to one skilled in the art.

For example, the control may be arranged to raise the pressure in the lower pressure rectification column 16A and hence the higher pressure rectification column 14A if the recovery of methane instantaneously falls below 98.5% and the pressure drop in the column 14A rises. A fall in product methane recovery could be caused by the vapour loading of the higher pressure rectification column rising to a level too close to the flood point, thereby causing the degree of separation in the higher pressure rectification column 14A to be reduced with the result that the impurity level in the product streams formed in the lower pressure rectification column 16A is increased. Increasing the pressure in the lower pressure rectification column 16A by resetting of the valve 58A increases the pressure in the higher pressure rectification column 14A thus reducing the vapour loading.

There is, however, another effect of an increasing mole fraction of nitrogen in the feed gas which, unlike its effect on the vapour loading of the column 14A, favours high recovery of methane product. This effect is that with increasing nitrogen mole fraction there is an increased flow of vapour from the top of the column 14A into the condensing passages of the condenser-reboiler 18A. Accordingly, more reflux is provided for the double rectification column. This makes it easier to separate the methane product. Under these conditions, the amount of nitrogen that is recycled from the lower pressure rectification column 16A to the higher pressure rectification column 14A can be reduced to keep down the power consumption of the recycle compressor. Such an adjustment can be made by changing the setting of the valve 52. The methane recovery may be used to control the valve 52 analogously to the valve 58A. The operator of the plant therefore has two parameters to employ in controlling the process, namely the size of the flow through the valve 52 and the pressure at the top of the lower pressure rectification column 16A.

It is preferred that the rate of recycle of nitrogen from the lower pressure column 16A to the higher pressure column 14A be at a maximum when the mole fraction of nitrogen in the feed gas stream is at a minimum. Provided that so doing does not move the higher pressure rectification column 14A too close to flood for product recovery to be maintained, it is normally preferred that the rate of recycle of nitrogen be progressively reduced as the mole fraction of nitrogen in the feed gas stream is increased. This is so as to minimise the power consumption of the method and apparatus according to the invention. One exception is if power is available particularly cheaply at the site where the method according to the invention is operated. It can then be advantageous to operate the higher pressure column 14A at a higher pressure, thus making separation more energy intensive therein, and recycle more nitrogen from the lower pressure column 16A to the higher pressure column 14A than would otherwise be necessary.

Typically, however, increasing the operating pressure of the rectification column 14A and 16A by resetting the valve 58A can with advantage be deferred until recycle of nitrogen has been reduced to a minimum. Typically, once the mole fraction of nitrogen in the feed gas has reached, say, 30% by volume, the passage of nitrogen through the inlet 56A is halted. It is still at such feed compositions desirable to continue to pass liquid nitrogen into the top of the higher pressure rectification column 14A via the expansion valve 54A so as to maintain a good match in the heat exchanger of the temperature-enthalpy profile of the streams being warmed with those being cooled. Accordingly, even if the inlet 56A is closed, it is preferred to maintain a sufficient flow of recycle gas through the recycle compressor 48 to enable liquid to pass from the expansion valve 54A to the higher pressure rectification column 14A at the requisite rate.

The higher pressure rectification column 14A cannot of course be operated at critical pressure or above. There is therefore a ceiling on the range of operating pressure for this column. Thus, it is not desirable to increase the operating pressure of the higher pressure rectification column 14A much above about 29 bar absolute. Accordingly, we prefer to ensure that the operating pressure of the lower pressure rectification column 16A does not exceed about 3.5 bar absolute at its top.

Even if operation of the higher pressure rectification column 14A is started at a low vapour loading, say, one from one half to three quarters of that at flood point, the final nitrogen mole fraction in the feed gas may be so high that it becomes impossible to maintain a methane recovery of 98.5% or more over the full operating life of the method and apparatus according to the invention. Accordingly, when the nitrogen mole fraction in the feed gas increases to at least a predetermined value, the second double rectification column 12B may be placed in communication with the phase separator 10 and the second column 12B operated in parallel with the first column 12A. The predetermined nitrogen mole fraction value depends on specific application and process needs. In one embodiment, the predetermined nitrogen mole fraction value is equal to 0.40.

The double rectification column 12B has typically substantially the same dimensions as the column 12A. Alternatively, it may be smaller or larger, the particular choice of size typically being made so as to optimise the cost of the plant. The double rectification column 12B shares the purification unit 2, the main heat exchanger 4, the phase separator 10, the valve 23, the heat exchanger 26, the recycle compressor 48, the valve 52 and the product compressor 60 with the double rectification column 12A. Its operation is analogous with that of the double rectification column 12A and therefore need not be described again. It should be noted that a part having a numerical reference followed by the letter B operates analogously to the part having the same numerical reference followed by the letter A. Typically, however, by the time the vapour loading on the higher pressure rectification column 14A has reached a level at which it becomes desirable to bring the double rectification column 12B on stream, the flow of nitrogen via the inlet 56A to the higher pressure rectification column 14A has ceased. As a result, it is not necessary to provide the corresponding column 14B with the inlet 56B, and this inlet can be omitted, if desired.

It is also possible to omit the pressure regulating valves 58A and 58B from the apparatus shown in the drawing and therefore to operate both the lower pressure rectification columns 16A and 16B at a constant top pressure.

What is claimed is:

1. A method of rejecting nitrogen from a feed gas stream comprising methane and nitrogen so as to form a methane product, the mole fraction of nitrogen in the feed gas increasing over a period of time, the method comprising cooling the feed gas stream in a main heat exchanger, rectifying the cooled feed gas stream in a first double rectification column comprising a higher pressure rectification column, a lower pressure rectification column, and a condenser-reboiler placing the higher pressure rectification column in heat exchange relationship with the lower pressure rectification column, expanding at least part of the feed gas stream into the higher pressure rectification column, partially liquefying the feed gas stream upstream of the first double rectification column, and operating a second double rectification column in parallel with the first double rectification column when the nitrogen mole fraction in the feed gas stream has a mole fraction value of 0.4.

2. The method according to claim 1, wherein the operating pressure of the lower pressure rectification column is periodically increased.

3. The method according to claim 1 wherein the first recycle gas flow is compressed, is cooled in the main heat exchanger, is liquefied in the condenser-reboiler, and is introduced into the higher pressure rectification column of the first double rectification column.

4. The method according to claim 1, wherein a first flow of gas is passed as a first recycle gas flow from the lower pressure rectification column of the first double rectification column to the higher pressure rectification column of the first double rectification column, a product methane stream is withdrawn in liquid state from the lower pressure rectification column of the first double rectification column, is raised in pressure, and is vaporised at least in part in the main heat exchanger, and a second recycle gas flow is taken from the lower pressure rectification column of the first double rectification column, is compressed, is cooled in the main heat exchanger, and is introduced at least partly in liquid state into the top of the higher pressure rectification column of the first double rectification column.

5. The method according to claim 4, wherein the second recycle gas flow is compressed to a higher pressure than the first recycle gas flow.

6. The method according to claim 4, wherein the first and second recycle gas flows are compressed in a plural stage compressor, the second recycle flow being taken from a stage of the compressor downstream of a stage from which the first recycle flow is taken.

7. The method according to claim 1, wherein the pressure in the lower pressure rectification column of the first double rectification column is adjusted so as to maintain a constant percentage recovery of methane in the product gas.

8. Apparatus for rejecting nitrogen from a feed gas stream comprising methane and nitrogen so as to form a methane product, the apparatus comprising a main heat exchanger for cooling the feed gas stream, a double rectification column for rectifying the feed gas stream comprising a higher pressure rectification column, a lower pressure rectification column, a condenser-reboiler placing the higher pressure rectification column in heat exchange relationship with the lower pressure rectification column, and an expansion device downstream of the main heat exchanger communicating with the higher pressure rectification column, the expansion device being arranged for introducing a part of the feed gas stream into the higher pressure rectification column in liquid state, wherein there is a second double rectification column in parallel with the first double rectification column and there is a back pressure regulating valve associated with the lower pressure rectification column of the first double rectification column which back pressure regulating valve is operable to increase the pressure n said lower pressure rectification column.

9. The apparatus according to claim 8, characterised in that there is a back pressure regulating valve associated with the lower pressure rectification column of the first double rectification column, which back pressure regulating valve is operable to increase the pressure in said lower pressure rectification column.

10. The apparatus according to claim 8, characterised in that the back pressure regulating valve is able to be controlled so as to maintain a constant percentage recovery of methane in the product gas.

* * * * *